(12) United States Patent
Jin et al.

(10) Patent No.: US 8,163,815 B2
(45) Date of Patent: Apr. 24, 2012

(54) DENTAL RESIN COMPOSITION, METHOD OF MANUFACTURE, AND METHOD OF USE THEREOF

(75) Inventors: Shuhua Jin, Wallingford, CT (US); Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 393 days.

(21) Appl. No.: 12/408,373

(22) Filed: Mar. 20, 2009

(65) Prior Publication Data
US 2010/0240794 A1    Sep. 23, 2010

(51) Int. Cl.
*A61K 6/083* (2006.01)
*A61C 5/00* (2006.01)
*C08G 63/00* (2006.01)
*C08G 69/00* (2006.01)
*C08F 118/02* (2006.01)

(52) U.S. Cl. ............ 523/116; 523/118; 433/228.1; 528/272; 528/288; 528/297; 528/306; 526/319

(58) Field of Classification Search .......... 523/116; 433/228.1; 528/272, 288, 297, 306; 526/319
See application file for complete search history.

(56) References Cited

U.S. PATENT DOCUMENTS

| | | | |
|---|---|---|---|
| 3,066,112 A | 11/1962 | Bowen | |
| 3,194,784 A | 7/1965 | Bowen | |
| 3,926,906 A | 12/1975 | Lee, II et al. | |
| 4,052,280 A * | 10/1977 | McGinnis | 522/33 |
| 4,093,601 A * | 6/1978 | Kuehn | 526/227 |
| 4,096,223 A * | 6/1978 | Krall | 264/533 |
| 4,282,138 A * | 8/1981 | Kuehn | 523/512 |
| 4,544,359 A | 10/1985 | Waknine | |
| 4,547,531 A | 10/1985 | Waknine | |
| 4,659,751 A | 4/1987 | Bowen | |
| 5,276,068 A | 1/1994 | Waknine | |
| 5,444,104 A | 8/1995 | Waknine | |
| 5,876,210 A * | 3/1999 | Klee et al. | 433/226 |
| 6,013,694 A | 1/2000 | Jia et al. | |
| 6,270,562 B1 | 8/2001 | Jia | |
| 6,403,676 B1 | 6/2002 | Jia et al. | |
| 6,417,246 B1 | 7/2002 | Jia et al. | |
| 6,653,365 B2 | 11/2003 | Jia | |
| 6,673,958 B2 | 1/2004 | Tiba et al. | |
| 6,677,474 B2 | 1/2004 | Hamer et al. | |
| 6,787,629 B2 | 9/2004 | Jia et al. | |
| 2005/0192374 A1 | 9/2005 | Jia et al. | |
| 2008/0262119 A1 * | 10/2008 | Bouwman et al. | 521/137 |

FOREIGN PATENT DOCUMENTS

| | | |
|---|---|---|
| EP | 0104491 A1 | 4/1984 |
| EP | 0269187 A2 | 11/1987 |

OTHER PUBLICATIONS

Bette Hileman, Bisphenol A related biological concern: 1. JDR, biocompatability of hydroxylated metabodies of BisGMA and BFDGE, Bisphenol A Harms Mouse Eggs, Chemical & Engineering News, 81(14), Apr. 7, 2003.
Chemical used in food containers disrupts brain development, Topics: Health Issues, Dec. 5, 2005.
Dow, Tone 2221 Polyol, CAS Reg. No. 69089-45-8, Published Dec. 2001, 1 page.
ISO 4049, 2000

* cited by examiner

*Primary Examiner* — Tae H Yoon
(74) *Attorney, Agent, or Firm* — Cantor Colburn LLP

(57) ABSTRACT

Disclosed herein are curable (meth)acrylate resins for dental compositions obtained by reacting an anhydride with an alcohol or an amine to obtain a carboxy ester or a carboxy amide and reacting the carboxy ester or carboxy amide with a (meth)acrylate monomer comprising an epoxide group or an oxetane group.

20 Claims, No Drawings

DENTAL RESIN COMPOSITION, METHOD OF MANUFACTURE, AND METHOD OF USE THEREOF

BACKGROUND

In recent years, materials used for dental restorations have principally comprised methacrylate and acrylate resins referred to herein as "(meth)acrylate resins". Resinous materials of this type are disclosed, for example, in U.S. Pat. Nos. 3,066,112 to Bowen, 3,194,784 to Bowen, and 3,926,906 to Lee et al. Many of the (meth)acrylate resins used in dental restorations contain units derived from bisphenol A. A common dental resin (meth)acrylate monomer is the condensation product of bisphenol A and glycidyl methacrylate, 2,2'-bis[4-(3-methacryloxy-2-hydroxy propoxy)-phenyl]-propane (BisGMA). Another (meth)acrylate dental resin containing units derived from bisphenol A is ethoxylated bisphenol A dimethacrylate (EBPADMA).

Although present in many common (meth)acrylate resins, Bisphenol A has been linked to a variety of health concerns. It has been found to be present in the urine of 93-95% of adults and children studied. High bisphenol A levels are significantly associated with heart disease, diabetes, and abnormally high levels of certain liver enzymes in humans. It is an endocrine disruptor, and can mimic the body's own hormones, including estrogen, potentially causing adverse health affects.

The bisphenol A containing (meth)acrylate resins are used because of their desired properties including low shrinkage upon curing. Replacement of these resins with other, known (meth)acrylate dental resins, for example 1,6-hexanediol dimethacrylate (HDDMA) and tri(ethylene glycol) dimethacrylate do not adequately provide the desired properties for dental uses as the resulting cured compositions exhibit high shrinkage after polymerization. Therefore, there is a perceived need in the art for a dental resin that is free of units derived from bisphenol A while maintaining good shrinkage resistance, good modulus of rupture, low water absorption, and low water solubility.

SUMMARY

In one embodiment, a curable (meth)acrylate resin for dental composition comprises a compound according to Structure Ia or IIIa

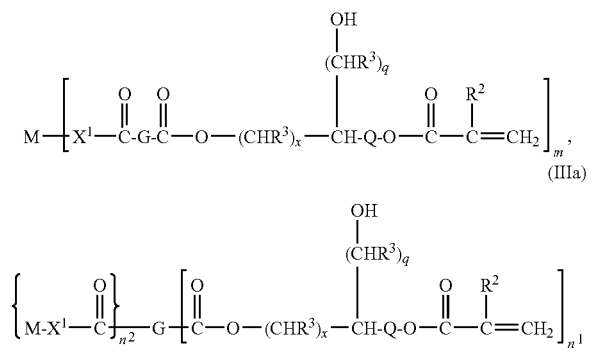

wherein M is substituted or unsubstituted alkyl, alkenyl, aryl, -alkylaryl, a polyester, a polyether, a polyurethane, a polycaprolactone group, or a combination comprising at least one of the foregoing groups; G is an aliphatic or aromatic hydrocarbyl group; $X^1$ is O or $-NR^1$; Q is substituted or unsubstituted $C_1$-$C_{16}$ alkylene, arylene, $-C_1$-$C_4$ alkyl-aryl-$C_1$-$C_4$ alkyl-, or polyether; $R^1$ is hydrogen, a substituted or unsubstituted alkyl, alkenyl, aryl, or -alkylaryl group; $R^2$ is H or methyl; each instance of $R^3$ is independently hydrogen or $C_1$-$C_{12}$ alkyl; x is 1 or 2; q is 0 or 1; m is 2, 3, 4, 5, or 6; $n^1$ is 1 or 2; and $n^2$ is 1 or 2, with the proviso that at least $n^1$ or $n^2$ is 2; wherein the curable (meth)acrylate resin is free of units derived from bisphenol A or bisphenol A analogs; and wherein the curable (meth)acrylate resin is a reaction product obtained by i) reacting an anhydride with an alcohol M(OH)$_p$ or an amine M(NR$^1$H)$_p$, wherein p=1, 2, 3, 4 or 5 to obtain a carboxy ester or a carboxy amide, and ii) reacting the carboxy ester or carboxy amide with a (meth)acrylate monomer comprising an epoxide group or an oxetane group to obtain a curable (meth)acrylate resin.

In another embodiment, a method of making a curable (meth)acrylate resin for dental compositions comprises i) reacting an anhydride with an alcohol M(OH)$_p$ or an amine M(NR$^1$H)$_p$, wherein p=1, 2, 3, 4, 5, or 6, M is substituted or unsubstituted alkyl, alkenyl, aryl, -alkylaryl, a polyester, a polyether, a polyurethane, a polycaprolactone group, or a combination comprising at least one of the foregoing groups, and $R^1$ is hydrogen, a substituted or unsubstituted alkyl, alkenyl, aryl, or -alkylaryl group to obtain a carboxy ester or a carboxy amide; and ii) reacting the carboxy ester or carboxy amide with a (meth)acrylate monomer comprising an epoxide group or an oxetane group to obtain a curable (meth)acrylate resin according to Structure Ia or IIIa

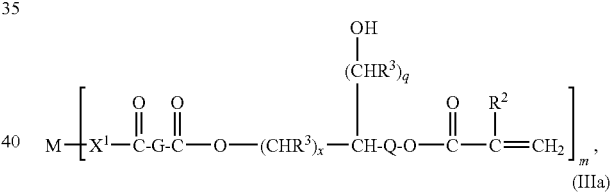

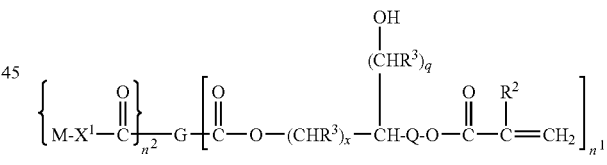

wherein M is substituted or unsubstituted alkyl, alkenyl, aryl, -alkylaryl, a polyester, a polyether, a polyurethane, a polycaprolactone group, or a combination comprising at least one of the foregoing groups; G is an aliphatic or aromatic hydrocarbyl group; $X^1$ is O or $-NR^1$; Q is substituted or unsubstituted $C_1$-$C_{16}$ alkylene, arylene, $-C_1$-$C_4$ alkyl-aryl-$C_1$-$C_4$ alkyl-, or polyether; $R^1$ is hydrogen, a substituted or unsubstituted alkyl, alkenyl, aryl, or -alkylaryl group; $R^2$ is H or methyl; each instance of $R^3$ is independently hydrogen or $C_1$-$C_{12}$ alkyl; x is 1 or 2; q is 0 or 1; m is 2, 3, 4, 5, or 6; $n^1$ is 1 or 2; and $n^2$ is 1 or 2, with the proviso that at least $n^1$ or $n^2$ is 2; wherein the curable (meth)acrylate resin is free of units derived from bisphenol A or bisphenol A analogs.

Other embodiments include a dental resin composition and a method of making a dental restoration.

These and other embodiments are described in further detail below.

DETAILED DESCRIPTION

It has now been found that a curable (meth)acrylate dental resin comprising the product of sequential reaction of an anhydride with an alcohol or an amine to form vicinal carboxy esters or vicinal carboxy amides, followed by reaction of the resulting vicinal carboxy esters or amides with an epoxy- or oxetane-functional (meth)acrylate are products suitable for use in dental resin compositions. In a specific embodiment, the curable (meth)acrylate dental resin is free of units derived from bisphenol A or analogs of bisphenol A. As used herein "bisphenol A or analogs thereof" means compounds according to the general structure below

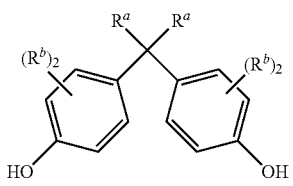

wherein each instance of $R^a$ is independently hydrogen or $C_{1-4}$ alkyl, and each instance of $R^b$ is hydrogen, $C_{1-4}$ alkyl, or halogen.

Surprisingly, the curable (meth)acrylate dental resin disclosed herein afford comparable or better modulus of rupture, water absorbance, water solubility, and shrinkage resistance when cured compared to bisphenol A-based dental compositions. The curable (meth)acrylate dental resin that is free of bisphenol A can be used in restorative dentistry, including use as dental adhesives, dental cements, dental filling/repairing materials, root canal sealants, crown and bridge materials, and the like.

Disclosed herein is a low shrinkage, curable (meth)acrylate dental resin for dental compositions that is a reaction product obtained by reacting a mono- or dianhydride with an alcohol or an amine, optionally in the presence of a catalyst, to obtain a carboxy ester or a carboxy amide, wherein the mole percent of alcohol or amine to anhydride groups is about 25 to about 100 mol %, specifically about 35 to about 90, more specifically about 50 to about 80, and yet more specifically about 55 to about 70 mol %; and then reacting the carboxy ester or carboxy amide with a (meth)acrylate monomer comprising an epoxide group or an oxetane group to result in the curable (meth)acrylate dental resin.

The curable (meth)acrylate dental resin can be made in two steps. In the reaction of an alcohol with an anhydride, the anhydride ring is opened to form a compound with vicinal carboxylic acid and ester groups, referred to herein as a carboxy ester. In the reaction of an amine with an anhydride, the anhydride ring is opened to form a compound with vicinal carboxylic acid and amide groups, referred to herein as carboxy amides. The second step is the reaction of the carboxy ester or carboxy amide with an ethylenically unsaturated compound comprising an epoxy group or an oxetane group. The carboxy group is esterified by a ring-opening reaction with the epoxide or oxetane to form an alcohol. The term anhydride as used herein refers to collectively to monoanhydrides, dianhydrides, and polyanhydrides. The term alcohol as used herein refers collectively to monoalcohols, diols, triols, tetraols, and polyols. The term amine as used herein refers collectively to monoamines, diamines, triamines, tetramines, and polyamines.

A wide variety of anhydrides can be used to prepare the curable (meth)acrylate dental resin. Suitable anhydrides can have the general structure $G-A_a$ where A is an anhydride group; a is an integer of 1, 2, or 3; and G is an unsubstituted or substituted hydrocarbyl group that is aliphatic or aromatic. Suitable aromatic groups are aryl (e.g., phenyl and naphthyl), and suitable aliphatic groups are alkyl, alkenyl, or alkynyl groups. Suitable substituents on G include halogen, cyano, hydroxyl, nitro, azido, alkanoyl (acyl), carboxyl, carboxamido, alkyl, alkenyl, alkynyl, alkoxy, aryloxy, alkylthio, alkylsulfinyl, alkylsulfonyl, aminoalkyl, aryl, alkylaryl, arylalkoxy, and aromatic heterocyclic.

Examples of suitable monoanhydrides include succinic, maleic, itaconic, glutaric, 1,1-cyclohexane diacetic, phthalic, tetrahydrophthalic, hexahydrophthalic, methyltetrahydrophthalic, trimellitic, nadic, methyl nadic, phenylmaleic, and citraconic anhydride, or the like, or a combination comprising at least one of the foregoing monoanhydrides. Examples of dianhydrides include pyromellitic dianhydride (PMDA, 1,2,4,5-benzenetetracarboxylic dianhydride), 3,3',4,4'-benzophenone tetracarboxylic dianhydride (BTDA), and biphenyl tetracarboxylic dianhydride (BPDA), or the like, or combinations comprising at least one of the foregoing dianhydrides. Examples of polyanhydrides are maleic anhydride copolymers, maleic anhydride graft polymers, or polyisoprene-graft maleic anhydride, or the like, or a combination comprising at least one of the foregoing polyanhydrides.

Any alcohol having of general structure $M(OH)_p$ wherein p=1, 2, 3, 4, 5, 6, or greater can be used for reaction with the anhydride. M can be an unsubstituted or substituted alkyl, alkenyl, aryl, -alkylaryl group, a polyester, a polyether, a polyurethane, or a polycaprolactone group, or the like, or a combination comprising at least one of the foregoing groups. In one embodiment, $M(OH)_p$ where p=2 is not bisphenol A or analogs thereof, or does not contain units of bisphenol A or analogs thereof. Suitable substitution on M include halogen, cyano, nitro, azido, alkanoyl (acyl), carboxamido, alkyl, alkenyl, alkynyl, alkoxy, aryloxy, alkylthio, alkylsulfinyl, alkylsulfonyl, aminoalkyl, aryl, alkylaryl, arylalkoxy, and aromatic heterocyclic.

Suitable alcohols having the general structure $M(OH)_p$ in which p=1 (monoalcohols) include those alcohol wherein M is $C_1-C_{16}$ alkyl, aryl, or $-C_1-C_4$ alkyl-aryl. Exemplary monoalcohols include methanol, ethanol, 1-butanol, 2-propanol, 2-methyl-1-propanol, 2-butanol, 2-methyl-1-butanol, cyclohexanol, benzyl alcohol, 1-phenethyl alcohol, 2-phenethyl alcohol, 2-phenyl-1-propanol, piperonyl alcohol, and phenol.

Suitable alcohols having the general structure $M(OH)_p$ in which p=2 (diols) include those diols where M is divalent $C_1-C_{20}$ alkylene, arylene, or $-C_1-C_4$ alkyl-aryl-$C_1-C_4$ alkyl-. Exemplary diols include diethylene glycol, triethylene glycol, neopentyl glycol, 2,2-diethyl-1,3-propanediol, 2-ethyl-2-butyl-1,3-propanediol, cyclohexanedimethanol, 1,3-propanediol, 1,5-pentanediol, 1,6-hexanediol, 1,10-decanediol, 1,12-dodecanediol, 1,14-tetradecanediol, and 1,16-hexadecanediol.

Exemplary alcohols having the general structure $M(OH)_p$ in which p=3 (triols) include glycerol, trimethylolpropane, and trimethylolethane. An example of an alcohol having the general structure $M(OH)_p$ in which p=4 (tetraol) is pentaerythritol.

The alcohol $M(OH)_p$ can be oligomeric or polymeric. Examples of oligomeric or polymeric alcohols include polyester, polycarbonate, polyurethane, and polycaprolactone polyols. Specific examples of polyester polyols are ETERNACOLL® 3010, 3015, 3030, 5010, and 5011, available from UBE America, Inc. A specific example of a polycarbonate polyol is UC-CARB 100 (Poly(oxycarbonyloxymethylene-1,4-cyclohexanediylmethylene) CAS Reg. No. 26894-28-0; 2 hydroxyl groups per molecule), also available from UBE America, Inc. A specific example of a polycaprolactone polyol is TONE® Polyol 2241 (CAS Reg. No. 69089-45-8; 2 hydroxyl groups per molecule), available from Dow Chemicals.

Any amine of general structure $M(NR^1H)_p$ wherein p=1, 2, 3, 4, 5, 6, or greater can be used for reaction with the anhydride. M can be an unsubstituted or substituted, alkyl, alkenyl, aryl, alkylaryl, a polyester, a polyether, a polyurethane, a polycaprolactone group, or the like, or a combination comprising at least one of the foregoing groups. $R^1$ can be hydrogen, a substituted or unsubstituted alkyl, alkenyl, aryl, or -alkylaryl group. Suitable substituents for $R^1$ include hydrogen, alkyl, alkenyl, alkynyl, aryl, alkylaryl, arylalkoxy, and aromatic heterocyclic.

Suitable amines having the general structure $M(NR^1H)_p$ in which p=1 (monoamines) those amines where M is $C_1$-$C_{16}$ alkyl, aryl, or —$C_1$-$C_4$ alkyl-aryl. Exemplary monoamines include methylamine, 1-aminoethane, and 1-aminobutane.

Suitable amines having the general structure $M(NR^1H)_p$ in which p=2 (diamines) are diamines where M is divalent $C_1$-$C_{16}$ alkylene, arylene, or —$C_1$-$C_4$ alkyl-aryl-$C_1$-$C_4$ alkyl-. An exemplary diamine is 1,6-hexanediamine.

In the process to prepare the vicinal carboxy esters or carboxy amides, an anhydride and an alcohol or amine are mixed for a period of time at elevated temperature, to form intermediate vicinal carboxy esters or carboxy amides, respectively. The reaction takes place at elevated temperature, for example from about 50 to about 250° C., specifically from about 80 to about 200° C., and more specifically from about 100 to about 140° C.

The use of Lewis acid or tertiary amine catalysts can be used to accelerate the reaction. Examples of tin-containing catalysts are stannous octoate, stannous 2-ethylhexanoate, dibutyltin dilaurate, dibutyltin maleate, dibutyltin diacetate, dioctyltin maleate, dibutyltin phathalate, stannous naphthenate, stannous stearate, dibutyltin diacetylactonate, dibutyltin oxide, or the like, or a combination comprising at least one of the foregoing tin-containing catalysts. Examples of tertiary amine catalysts are triethylamine, and dimethylaminobenzene.

The catalyst can be used in an amount of about 0.10 to about 10 mole percent based on the moles of reactant, specifically about 1 to about 8 mol percent, more specifically about 2 to about 7 mol percent, and yet more specifically about 3 to about 6 mole percent based on the moles of reactant.

In the reaction to form curable (meth)acrylate dental resin from the carboxy esters or carboxy amides, a (meth)acrylate monomer comprising an epoxide group or an oxetane group is reacted with the carboxy ester or carboxy amide, optionally in the presence of a catalyst. The carboxy group is esterified by a ring-opening reaction with the epoxide or oxetane to form an alcohol. Suitable (meth)acrylate monomer containing an epoxide or oxetane group for reaction with the carboxy ester or carboxy amide include those of structure,

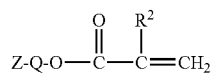

where Z is an epoxide or an oxetane group; Q is divalent linking group; and $R^2$ is hydrogen or methyl. Q can include linking groups including unsubstituted or substituted $C_1$-$C_{16}$ alkylene, arylene, —$C_1$-$C_4$ alkyl-aryl-$C_1$-$C_4$ alkyl-, polyether, and the like. Substituents for Q include halogen, cyano, hydroxyl, nitro, azido, alkanoyl (acyl), carboxamido, alkyl, alkenyl, alkynyl, alkoxy, aryloxy, alkylthio, alkylsulfinyl, alkylsulfonyl, aminoalkyl, aryl, alkylaryl, alkylaryl, arylalkoxy, and aromatic heterocyclic.

A specific example of a (meth)acrylate monomer comprising an epoxide group is glycidyl methacrylate (GMA). An example of a (meth)acrylate monomer comprising an oxetane group is a (3-ethyl-3-oxetanyl)methyl methacrylate, commercially available under the trade name ETERNACOLL® OXMA from UBE America, Inc.

The epoxide/oxetane ring opening reaction can take place at elevated temperatures, for example from about 50 to about 250° C., specifically from about 80 to about 200° C., and more specifically from about 100 to about 140° C.

The use of a catalyst can be used to accelerate the ring-opening reaction. Examples of suitable catalysts are tin-containing and titanium-containing catalysts. Examples of tin-containing catalysts are stannous octoate, stannous 2-ethylhexanoate, dibutyltin dilaurate, dibutyltin maleate, dibutyltin diacetate, dioctyltin maleate, dibutyltin phathalate, stannous naphthenate, stannous stearate, dibutyltin diacetylactonate, dibutyltin oxide, or the like, or a combination comprising at least one of the foregoing tin-containing catalysts. Examples of titanium-containing catalysts are tetrabutyl titaniate, tetrapropyl titanate, tetraisopropyl titanate, triethanolamine titanate, titanium tetraacetylacetonate, or the like, or a combination comprising at least one of the foregoing titanium-containing catalysts.

The ring-opening catalyst can be used in an amount of about 0.10 to about 10 mole percent based on the moles of reactant, specifically about 1 to about 8 mol percent, more specifically about 2 to about 7 mol percent, and yet more specifically about 3 to about 6 mole percent based on the moles of the reactants.

In one embodiment, the curable (meth)acrylate dental resin is of structure Ia.

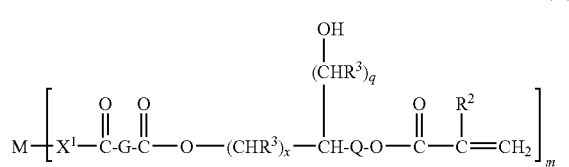

wherein M and G are as previously described; $X^1$ is O or —$NR^1$; $R^1$ can be hydrogen, a substituted or unsubstituted alkyl, alkenyl, aryl, or -alkylaryl group; $R^2$ is H or methyl; each instance of $R^3$ is independently hydrogen or $C_1$-$C_{12}$ alkyl; x is 1 or 2; q is 0 or 1; Q is substituted or unsubstituted $C_1$-$C_{16}$ alkylene, arylene, —$C_1$-$C_4$ alkyl-aryl-$C_1$-$C_4$ alkyl-, or polyether; and m is an integer of 1, 2, 3, 4, 5, or 6.

In another embodiment, the curable (meth)acrylate dental resin is of structure Ib.

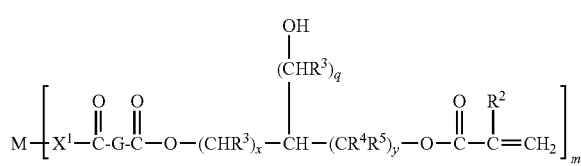

wherein M, $X^1$, G, x, $R^3$, q, and $R^2$ are as previously described; $R^4$ and $R^5$ are each independently hydrogen, or $C_1$-$C_{12}$ alkyl; and y is an integer of 1, 2, 3, 4, 5, 6, 7, or 8.

Exemplary curable (meth)acrylate dental resins according to structure Ia include those of structure II.

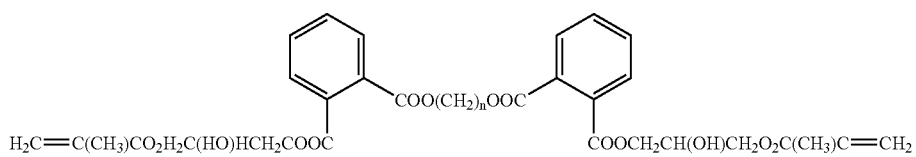

(II)

wherein n is 1 to about 20, specifically about 3 to about 14, and more specifically about 6 to about 10.

In one embodiment, the curable (meth)acrylate dental resin is of structure IIIa

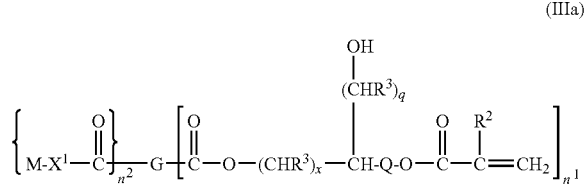

(IIIa)

wherein M, $X^1$, G, Q, $R^2$, $R^3$, $R^4$, $R^5$, x, y, and q have been previously described and wherein $n^1$ is 1 or 2 and $n^2$ is 1 or 2; specifically wherein at least one of $n^1$ and $n^2$ is 2; and more specifically wherein both $n^1$ and $n^2$ is 2.

In one embodiment, the curable (meth)acrylate dental resin is of structure IIIb

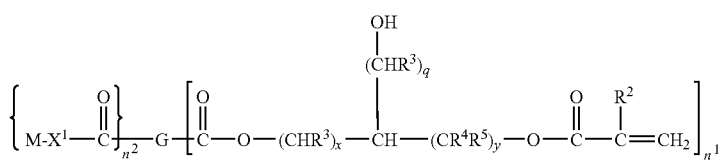

(IIIb)

wherein M, $X^1$, G, $R^2$, $R^3$, $R^4$, $R^5$, x, y, and q have been previously described and wherein n is 1 or 2 and $n^2$ is 1 or 2; specifically wherein at least one of $n^1$ and $n^2$ is 2; and more specifically wherein both $n^1$ and $n^2$ is 2.

An exemplary curable (meth)acrylate dental resin according to structure IIIa includes structure IV.

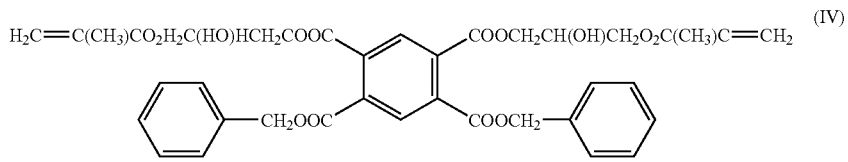

(IV)

As used herein, "alkyl" includes straight chain, branched, and cyclic saturated aliphatic hydrocarbon groups, having the specified number of carbon atoms, generally from 1 to about 36 carbon atoms for the straight chain and generally from 3 to about 20 carbon atoms for the branched and cyclic. Examples of alkyl include, but are not limited to, methyl, ethyl, n-propyl, isopropyl, n-butyl, 3-methylbutyl, t-butyl, n-pentyl, sec-pentyl, cyclopentyl, cyclohexyl, and octyl. Specific alkyl groups include lower alkyl groups, those alkyl groups having from 1 to about 8 carbon atoms, from 1 to about 6 carbon atoms, or from 1 to about 4 carbons atoms.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, anthracene, pentacene, fluorene, and bi-phenyl.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, -alkylphenyl is attached through carbon of the alkyl group.

In another embodiment, a dental resin composition comprises the curable (meth)acrylate dental resin, co-polymerizable ethylenically unsaturated monomer or oligomer, and a polymerization initiator. The dental resin composition optionally comprises diluent monomers, a polymerization accelerator, UV absorbers, or combinations comprising at least one of the foregoing materials. A filler can be added to the dental resin composition to form a dental composite composition that can be used as an adhesive, dental cement, dental filling/repairing material, root canal sealing/filling material, other crown and bridge materials, provisional crown and bridge materials, and the like. In a dental composite composition, the dental resin composition, when cured, forms a hard matrix encapsulating and binding the filler particles together.

Dental resin compositions prepared from the curable (meth)acrylate dental resin exhibit very low shrinkage upon cure. The dental resin compositions have a shrinkage after cure of less than 4 volume percent as measured by the mercury dilatometer, an instrument and method developed by NIST/ADA Health Foundation, specifically less than 3, more specifically less than 2, and yet more specifically less than 1.5.

The curable (meth)acrylate dental resin can be used in an amount of about 1 to about 99 weight percent (wt %) based on the total weight of the polymerizable components, specifically about 10 to about 95 wt %, more specifically about 30 to about 90 wt %, and yet more specifically about 50 to about 80 wt % based on the total weight of the polymerizable components.

A co-polymerizable ethylenically unsaturated monomer or oligomer can be used in combination with the curable (meth) acrylate dental resin to provide a dental restorative material. The co-polymerizable ethylenically unsaturated monomer or oligomer can contain a reactive functionality that is copolymerizable with the curable resins, including (meth)acrylate, epoxide, (meth)acrylamide, vinyl, allyl, or other ethylenically unsaturated functionality. Non-limiting examples of co-polymerizable ethylenically unsaturated monomer or oligomer include urethane dimethacrylate (UDMA), polyurethane dimethacrylate (PUDMA), diurethane dimethacrylate (DUDMA), polycarbonate dimethacrylate (PCDMA), or the like or a combination comprising at least one of the foregoing. PCDMA is disclosed in U.S. Pat. Nos. 5,276,068 and 5,444,104 to Waknine. It is the condensation product of two parts of a hydroxyalkylmethacrylate and 1 part of a bis(chloroformate). In one embodiment, the co-polymerizable ethylenically unsaturated monomer or oligomer has a viscosity of greater than 0.1 Pa-second, more typically greater than about 1 Pa-second, at 23° C.

The co-polymerizable ethylenically unsaturated monomer or oligomer can be used in an amount of about 1 to about 70 wt % based on the total weight of the polymerizable components, specifically about 5 to about 50 wt % and yet more specifically about 10 to about 20 wt %.

A polymerization initiator can be used in combination with the curable (meth)acrylate dental resin. Polymerization initiators can be light (ultraviolet or visible light) activated, or heat activated. Polymerization initiators that are light activated are referred to as photoinitiators. Examples of suitable photoinitiators include benzil, benzoin, benzoin methyl ether, dl-camphorquinone (CQ), 2,4,6-trimethylbenzoyldiphenylphosphine oxide (L-TPO), and substituted benzil diketones. The amount of photoinitiator is selected according to the curing rate desired. A minimal catalytically effective amount is generally about 0.01 wt % of the total dental resin composition, and will lead to a slower cure. Faster rates of cure are achieved with amounts of photoinitiator of about 0.01 to about 5 wt % based on the total dental resin composition.

Alternatively, heat activated, or thermal, polymerization initiators can be used. Use of these initiators affords self-curing composite dental materials that do not require the use of UV or visible light for initiation. Examples of thermal polymerization initiators are lauryl peroxide, tributyl hydroperoxide and benzoyl peroxide (BPO). Thermal initiators can be used in an amount of about 0.01 to about 1.0 wt % of the total dental resin composition.

Polymerization accelerators are used in combination with polymerization initiators, and are generally tertiary amines. Examples of polymerization accelerators used in combination with photoinitiators are dimethylaminoethyl methacrylate, diethylaminoethyl methacrylate (DEAEMA), and ethyl 4-(dimethylamino)benzoate (EDMAB). These polymerization accelerators are used in an amount of about 0.05 to about 2.0 wt % of the total dental resin composition. Aromatic tertiary amines are generally used in combination with thermal initiators. Examples of polymerization accelerators generally used with thermal initiators are EDMAB, 2-[4-(dimethylamino)phenyl]ethanol, N,N-dimethyl-p-toluidine (DMPT), and bis(hydroxyethyl)-p-toluidine (DHEPT). These polymerization accelerators are generally used in an amount of about 0.5 to about 4.0 wt % of the total dental resin composition.

Diluent monomers can be used to increase the surface wettability of the dental resin composition and/or to decrease the viscosity of the dental resin composition. Examples of diluent monomers are hydroxyalkyl (meth)acrylates, 2-hydroxyethyl (meth)acrylate, 2-hydroxypropyl (meth)acrylate, 4-hydroxybutyl (meth)acrylate, ethylene glycol (meth)acrylate, diethylene glycol (meth)acrylate, tri(ethylene glycol) di(meth)acrylate, tri(ethylene glycol) dimethacrylate (TEGDMA), tetra(ethylene glycol) di(meth)acrylate, di(meth)acrylates, 1,4-butanediol di(meth)acrylate, dodecane diol di(meth)acrylate, 1,6-hexanediol di(meth)acrylate, 1,6-hexanediol dimethacrylate (HDDMA), polyethylene glycol mono(meth)acrylate, glycerol di(meth)acrylate, trimethylolpropane di(meth)acrylate, pentaerythritol tri(meth) acrylate, the (meth)acrylate of phenyl glycidyl ether, or the like, or a combination comprising at least one of the foregoing diluent monomers. Such diluent monomers can have a viscosity of less than 0.1 Pa-second, more typically less than about 0.05 Pa-second, at 23° C.

Diluent monomers, when present, are used in an amount of about 1 to about 70 wt % of the total polymerizable components, specifically about 5 to about 50 wt %, and more specifically about 10 to about 25 wt %.

Ultraviolet (UV) absorbers can optionally be used. UV absorbers serve to reduce discoloration of the dental resin composition resulting from exposure to UV light. Suitable UV absorbers are benzophenones, benzotriazoles, or the like, or a combination of both. Examples of UV absorbers are CYASORB® UV-9, UV-24, UV-531, and UV-5411, available from Cytec Industries, and TINUVIN® P, available from Ciba Specialty Chemicals, or the like, or combinations comprising at least one of the foregoing UV absorbers. A UV absorber, when present, can be used in an amount of about 0.05 to about 5.0 wt % of the total dental resin composition.

In another embodiment, the composition comprises a filler to afford a dental composite composition. The filler can be covalently bonded to the curable resin itself or to a coupling agent (e.g., a silane) that is covalently bonded to both. Examples of fillers are silica, quartz, strontium silicate, strontium borosilicate, lithium silicate, lithium alumina silicate, amorphous silica, ammoniated or deammoniated calcium phosphate, tricalcium phosphate, alumina, zirconia, tin oxide, titania, or the like, or a combination comprising at least one of the foregoing fillers. Some of the aforementioned fillers and methods of preparation thereof are known in the art, as disclosed in U.S. Pat. Nos. 4,544,359 and 4,547,531 to Waknine, pertinent portions of which are incorporated herein by reference. Hybrid organic-inorganic fillers can also be used. An example of a hybrid organic-inorganic filler is a polyhedral oligomeric silsesquioxanes (POSS), available from Hybrid Plastics. POSS can be incorporated into dental composite compositions as disclosed in U.S. Pat. No. 6,653,365. Nano sized silica particles as disclosed in U.S. Pat. Nos. 6,417,246 and 6,787,629 to Jia et al. can also be used. Zirconium methacrylate and zirconium dimethacrylate, available from Geleste, Inc. under the product codes of CXZR050 and CXZR051, can also be used. High refractive index fillers can also be used. Examples of high refractive index fillers are silica glass fillers; calcium silicate based fillers, apatites, hydroxyapatites, modified hydroxyapatites, or the like, or a combination comprising at least one of the foregoing high refractive index fillers. Alternatively, inert, non-toxic, radiopaque materials such as bismuth oxide ($Bi_2O_3$), bismuth oxychloride, zirconium oxide, barium sulfate, and bismuth subcarbonate in micro- or nano-scaled sizes may be used. In addition, fibrous fillers such as those disclosed in U.S. Pat. Nos. 6,013,694, 6,403,676 and 6,270,562 to Jia and Jia et al. can be used.

The fillers can be treated with a silane-coupling agent to increase adhesion with the dental resin composition. Silane treated fumed silica based on Aerosil A200 is available from Degussa Corp under the trade names of AEROSIL® R711 and R7200. The fillers have particle sizes of about 0.01 to about 5.0 micrometers, and can further comprise bound or unbound silicate colloids of about 0.001 to about 0.2 micrometers.

The total amount of filler in the dental composite composition can vary from about 1 to about 90 wt % based on the total weight of the dental composite composition. The amount used is determined by the requirements of the particular application. Thus, for example, crown and bridge materials generally comprise about 60 to about 90 wt % filler; luting cements and root canal sealers comprise about 20 to about 80 wt % filler; lower viscosity materials such as tooth surface sealants and adhesives generally comprise 0 to about 30 wt % filler; and restorative materials comprise about 50 to about 90 wt % filler, with the remainder in all cases being the dental resin composition comprising the curable resin.

In another embodiment, the curable (meth)acrylate dental resin is formulated into a dental composite composition for dental restorative work by mixing with a co-polymerizable ethylenically unsaturated monomer or oligomer, polymerization initiator, polymerization accelerator, filler, and optionally diluent monomer, UV absorber, or a combination comprising at least one of the foregoing materials. After the damaged tooth is appropriately prepared, the dental composite composition thus obtained is placed on the tooth, and cured. Curing can be initiated through the use of UV or visible light, or in the case of self-curing dental composite compositions, by the inherent warmth of the mouth. When necessary, two or more layers of dental composite composition can be sequentially applied and cured.

In a variation of the aforementioned method, the dental composite composition may be formulated as a two-part system, wherein the first part comprises the curable (meth)acrylate dental resin, co-polymerizable ethylenically unsaturated monomer or oligomer, and filler; and the second part comprises the polymerization initiator, polymerization accelerator, and diluent monomer. The two parts are metered out and mixed using a spatula as needed.

The curable (meth)acrylate dental resin comprising the product of sequential reaction of an anhydride with an alcohol or an amine to form vicinal carboxy esters or vicinal carboxy amides, followed by reaction of the resulting carboxy esters or amides with epoxy- or oxetane-functional (meth)acrylates can replace bisphenol A-based curable resins in dental composite compositions. The risk of possible adverse health effects from leaching of bisphenol A from the dental composite compositions when used in the human oral cavity is thereby eliminated. Furthermore, the dental composite compositions containing the curable (meth)acrylate dental resin afford comparable or better flexural strength, water absorbance, water solubility, and shrinkage resistance compared to common bisphenol A-containing dental composite compositions.

Exemplary curable (meth)acrylate dental resins, method of manufacture, and method of use thereof will now be described by example. The examples are set forth as representative. They are not to be construed as limiting the scope of the invention as these and other equivalent embodiments will be apparent in view of the present disclosure and appended claims.

EXAMPLES

Example 1

Synthesis of Curable (meth)acrylate Dental Resin of Structure II, n=6

1,6-Hexanediol (HD, 59 g, 0.5 mol) was heated to 120° C. in a flask until melted. Triethyl amine (TEA, 0.5 g) was then added with stirring. Phthalic anhydride (PTA, 148 g, 1 mol) was slowly added, and stirring was continued at 120° C. The reaction was monitored by Fourier transform infrared spectroscopy (FTIR) and considered finished when the anhydride peak at 1784 $cm^{-1}$ disappeared. Then, glycidyl methacrylate (GMA, 142 g, 1 mol) was slowly added, and stirring was continued at 120° C. until the epoxy peak at 910 $cm^{-1}$ in the FTIR spectrum disappeared. The product was a clear colorless liquid.

Example 2

Synthesis of Curable (meth)acrylate Dental Resin of Structure II, n=10

The synthetic procedure is the same as that of Example 1, except 1,10-decanediol (87 g, 0.5 mol) was used in place of 1,6-hexanediol. The product was a clear colorless liquid.

Example 3

Synthesis of Curable (meth)acrylate Dental Resin IV

Benzyl alcohol (108 g, 1 mol) and 1,2,4,5-benzenetetracarboxylic dianhydride (109 g, 0.5 mol) were mixed in a flask and heated to 120° C. TEA (0.5 g) was added, and mixing was continued at 120° C. until the anhydride peak at 1784 $cm^{-1}$ in the FTIR spectrum disappeared. GMA (142 g, 1 mol) was then slowly added, and mixing was continued at 120° C. until the epoxy peak at 910 $cm^{-1}$ disappeared. The final resin was a clear, slightly yellowish liquid.

Example 4

Curable Resin Properties

The physical properties of the curable (meth)acrylate dental resins of Examples 1, 2, and 3 in comparison with Bis-GMA and other common resins used in dental composite material are listed in Table 1. Viscosities were measured at 40° C. or 22° C. using a RM180 Rheomat (Rheometric Scientific) rheometer. The refractive indices were measured at 22° C. using a refractometer from Milton Ray Co. Polymerization shrinkage (vol %) was measured by mercury dilatometer as developed by NIST. Each individual resin was mixed with a photo-curing system of CQ (0.2%), EDMAB (0.5%) and 2,4,6-trimethylbenzoyldiphenylphosphine oxide (0.5%, L-TPO). For the polymerization shrinkage test, each resin was blended with a fumed silica OX-50 (Degussa Corp.). The amount of fumed silica needed is dependent on the resin viscosity. The resin polymerization shrinkage reported in the table 1 below was calculated using the measured shrinkage of the resin/OX-50 composite dividing the vol % of resin used in the composite.

TABLE 1

Physical Properties of Curable Resins

| Curable Resin | Formula Wt. | Approx. Viscosity (Pa · S) | Refractive index | Shrinkage (vol %) |
|---|---|---|---|---|
| Example 1 | 698 | 344 | 1.5285 | 3.55 |
| Example 2 | 754 | 83 | 1.5228 | 3.47 |
| Example 3 | 718 | 398 | 1.5524 | 2.63 |
| BisGMA | 512 | 409 | 1.5560 | 3.94 |
| EBPADMA* | 452 | 31 | 1.5380 | 4.35 |
| UDMA* | 470 | 152 | 1.4830 | 4.28 |
| PCDMA* | 462 | 0.17 | 1.4659 | 6.53 |
| HDDMA* | 254 | 0.011 | 1.4570 | 11.57 |
| TEGDMA* | 258 | 0.008 | 1.4590 | 10.86 |

*viscosity was measured at 22° C.

It can be seen from the results that, the Bisphenol A free resins of Example 1, 2 and 3 all have higher formula weight and yet have similar or lower viscosities than the BisGMA resin. Additionally, the resins of Examples 1-3 all have lower polymerization shrinkage values than the conventional resins of BisGMA, EBPADMA, UDMA, as well as diluents such as PCDMA, HDDMA and TEGDMA resins tested.

Example 5

Dental Composite Compositions

Each synthesized resin of Example 1, Example 2 and Example 3 was further mixed with a polycarbonate methacrylate (PCDMA) as disclosed in U.S. Pat. No. 5,276,068 to Waknine in a 70/30 weight ratio. The same photo-curing system of CQ (0.2%), EDMAB (0.5%) and 2,4,6-trimethylbenzoyldiphenylphosphine oxide (0.5%, L-TPO) was added to the resin mixtures. A dental composite composition was prepared from 23% of the resin mixture, 1% of a fumed silica, Aerosil R7200 (Degussa), and 76% by weight of a barium borosilicate glass filler, Schott glass 8235. Flexural strength (FS), water absorption (WA), water solubility (WS), and shrinkage of the dental composite compositions were tested according to ISO 4049. The dental composite compositions were cured using a CureLite (Pentron Corp.) curing box for 3 minutes and then stored at 37° C. in water for 24 hrs for flexural strength testing and 1 week for WA and WS testing. Shrinkage (vol %) was measured by mercury dilatometry as developed by NIST. The results are listed in Table 2 below along with some of commercial dental restorative composite materials.

TABLE 2

Dental Composite Composition Properties

| Resin composite materials | FS (MPa) N = 6 | WA/WS (μg/mm³/wk)† | Shrinkage (vol %) |
|---|---|---|---|
| Example 1 | 162 (9) | 18/6 | 1.61 |
| Example 2 | 143 (15) | 16/4 | 1.38 |
| Example 3 | 138 (6) | 16/5 | 1.81 |
| Simile (Pentron) | 120 (19)* | 16/3 | 2.31 |
| Esthet-X (Dentsply) | 110 (11)* | — | 2.26 |
| Filtek Z250 (3M/ESPE) | 147 (10)* | — | 2.11 |

*This flexural strength data was cited from a test report of July 2002 of John Powers, et al, of University of Texas Health Science Center at Houston, Dental Branch.
†Microgram/millimeter³/week.

As can be seen from Table 2, dental composite compositions comprising the curable (meth)acrylate dental resins of Examples 1, 2, and 3 provide equal or better FS, SA, WS, and lower polymerization shrinkage compared to some of the common bisphenol A-containing dental composite compositions.

Example 6

Low Shrinkage Composite (LS Composite) without Bisphenol A Structure

The resin of Example 2 and PCDMA were mixed in a 70/30 weight ratio. CQ (0.3%), EDMAB (0.5%) and L-TPO (0.5%) were added to the resin mixture. The resin mixture was then mixed with a nano-sized silica sol with 40% silica content in methanol solvent, MA-ST-M organosilicasol (Nissan Chemical Industries, Ltd.). The methanol solvent in MA-ST-M was evaporated at 40° C. under vacuum. The resin/nano-silica blend was further firmed with a glass filler of Schott 8235 to achieve a non-sticky putty consistency. The final LS composite composition contains 15.6% of resin, 4% of silica and 80.4% of the glass filler by weight. A non-methacrylate resin-based silorane containing commercial material, Filtek™ LS ("silorane low shrink", 3M ESPE, A2lot#8AK) was also tested and compared. Similar to Example 5 above, the FS, WA, WS, and the polymerization volume shrinkage of the two materials were tested. In addition, the depth of cure of the materials was also measured according to ISO 4049 specification, using a dental office curing light, Avante Halogen Curing Light (Pentron), for 20 seconds curing of the test materials on top surface. The properties are shown in Table 3.

TABLE 3

LS composites properties

| Composite | FS (MPa) | WA/WS (μg/mm³/wk) | Shrinkage (vol %) | Depth of Cure (mm) |
|---|---|---|---|---|
| LS composites | 144 (10) | 8/6 | 1.12 | 7.5 |
| Filtek ™ LS | 138 (12) | 14/6 | 1.34 | 4.5 |

The depth of cure for the experimental LS Composite is much higher that the comparative low shrink resin. Improved depth of cure facilitates the bulk filling technique in a tooth filling/repairing application while avoiding large polymerization shrinkage.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. "Or" means and/or. Recitation of ranges of values herein are merely intended to serve as a shorthand method of referring individually to each separate value falling within the range, unless otherwise indicated herein, and each separate value is incorporated into the specification as if it were individually recited herein. All ranges disclosed herein are inclusive and combinable.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A curable (meth)acrylate resin for dental compositions, comprising:
a compound according to Structure IIIa

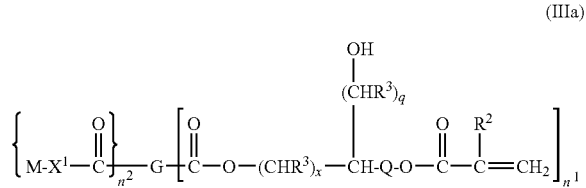

(IIIa)

wherein
M is selected from the group consisting of phenyl, $C_1$-$C_3$ alkylphenyl, and $C_5$-$C_{14}$ alkylene;
G is an aromatic hydrocarbyl group;
$X^1$ is O or —$NR^1$;
Q is substituted or unsubstituted $C_1$-$C_{16}$ alkylene, arylene, —$C_1$-$C_4$ alkyl-aryl-$C_1$-$C_4$ alkyl-, or polyether, wherein when Q is substituted, the substituents are selected from the group consisting of cyano, hydroxyl, nitro, azido, alkanoyl, carboxamido, alkyl, alkoxy, aryloxy, alkylthio, alkylsulfinyl, alkylsulfonyl, aminoalkyl, aryl, alkylaryl, arylalkoxy, aromatic heterocyclic, and combinations thereof;

$R^1$ is hydrogen, a substituted or unsubstituted alkyl, alkenyl, aryl, or -alkylaryl group, wherein when $R^1$ is substituted, substituents are selected from the group consisting of alkyl, aryl, alkylaryl, arylalkoxy, and aromatic heterocyclic;
$R^2$ is H or methyl;
each instance of $R^3$ is independently hydrogen or $C_1$-$C_{12}$ alkyl;
x is 1 or 2;
q is 0 or 1;
$n^1$ is 2; and
$n^2$ is 1 or 2;
wherein the curable (meth)acrylate resin is free of units derived from bisphenol A or bisphenol A analogs; and
wherein the curable (meth)acrylate resin is a reaction product obtained by
i) reacting an anhydride with an alcohol $M(OH)_p$ or an amine $M(NR^1H)_p$, wherein p=1, 2, 3, 4, 5 or 6 to obtain a carboxy ester or a carboxy amide, and
ii) reacting the carboxy ester or carboxy amide with a (meth)acrylate monomer comprising an epoxide group or an oxetane group to obtain a curable (meth)acrylate resin for dental compositions.

2. The curable (meth)acrylate resin of claim 1, comprising:
a compound according to Structure IIIb

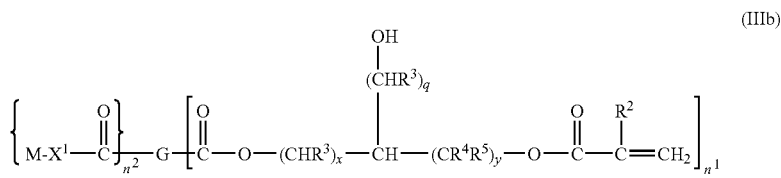

(IIIb)

wherein
G is phenyl;
$R^4$ and $R^5$ are each independently hydrogen, or $C_1$-$C_{12}$ alkyl; and
y is 1, 2, 3, 4, 5, 6, 7, or 8.

3. The curable (meth)acrylate resin of claim 1, comprising a compound according to Structure IV

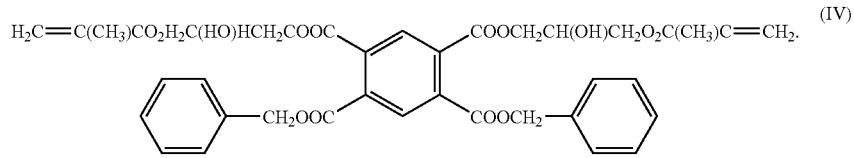

(IV)

4. The curable (meth)acrylate resin of claim 1, wherein the G group is derived from trimellitic anhydride, pyromellitic dianhydride, 3,3',4,4' benzophenone tetracarboxylic dianhydride, biphenyl tetracarboxylic dianhydride, or a combination of the foregoing anhydrides.

5. The curable (meth)acrylate resin of claim 1, wherein G is phenyl.

6. The curable (meth)acrylate resin of claim 1, wherein Q is $C_1$-$C_3$ alkylene.

7. The curable (meth)acrylate resin of claim 1, wherein $X^1$ is O.

8. A dental resin composition that exhibits low shrinkage upon cure comprising the curable resin of claim 1, a co-polymerizable ethylenically unsaturated oligomer, a polymerization initiator for speeding the cure, an optional polymerization accelerator, an optional filler, and an optional diluent monomer, wherein the curable resin is present in an amount of about 50 to about 99 weight percent based on the total weight of polymerizable components.

9. The dental resin composition of claim 8, wherein the polymerizable ethylenically unsaturated monomer or oligomer is free of units derived from bisphenol A or bisphenol A analogs.

10. The dental resin composition of claim 8, having a shrinkage after cure of less than 4 volume percent as measured by mercury dilatometer.

11. The dental resin composition of claim 8, comprising filler and having a shrinkage after cure of less than 2 volume percent.

12. A method of making a dental restoration, comprising:
mixing a curable resin, a co-polymerizable ethylenically unsaturated monomer or oligomer, a polymerization initiator, an optional polymerization accelerator, an optional filler, and an optional diluent monomer to form a dental composition;
applying the dental composition to a tooth to be repaired; and
curing the dental composition, wherein the curable resin is a compound according to Structure IIIa

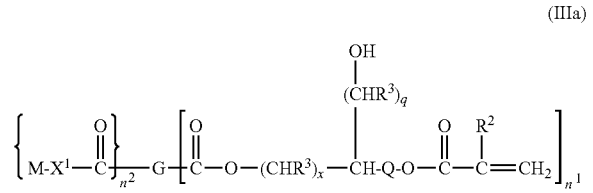

(IIIa)

wherein
M is selected from the group consisting of substituted or unsubstituted alkyl, alkenyl, aryl, -alkylaryl, a polyester, a polyether, a polyurethane, a polycaprolactone group, and combinations thereof, wherein when M is substituted, substituents are selected from the group consisting of cyano, nitro, azido, alkanoyl, carboxamido, alkyl, alkoxy, aryloxy, alkylthio, alkylsulfinyl, alkylsulfonyl, aminoalkyl, aryl, alkylaryl, arylalkoxy, aromatic heterocyclic, and combinations thereof;
G is an aromatic hydrocarbyl group;
$X^1$ is O or —$NR^1$;
Q is substituted or unsubstituted $C_1$-$C_{16}$ alkylene, arylene, —$C_1$-$C_4$ alkyl-aryl-$C_1$-$C_4$ alkyl-, or polyether, wherein when Q is substituted, the substituents are selected from the group consisting of cyano, hydroxyl, nitro, azido, alkanoyl, carboxamido, alkyl, alkoxy, aryloxy, alkylthio, alkylsulfinyl, alkylsulfonyl, aminoalkyl, aryl, alkylaryl, arylalkoxy, aromatic heterocyclic, and combinations thereof;
$R^1$ is hydrogen, a substituted or unsubstituted alkyl, alkenyl, aryl, or -alkylaryl group, wherein when $R^1$ is substituted, substituents are selected from the group consisting of alkyl, aryl, alkylaryl, arylalkoxy, and aromatic heterocyclic;
$R^2$ is H or methyl;
each instance of $R^3$ is independently hydrogen or $C_1$-$C_{12}$ alkyl;
x is 1 or 2;
q is 0 or 1;
$n^1$ is 2; and
$n^2$ is 1 or 2;
wherein the curable (meth)acrylate resin is free of units derived from bisphenol A or bisphenol A analogs; and
wherein the curable (meth)acrylate resin is a reaction product obtained by
i) reacting an anhydride with an alcohol $M(OH)_p$ or an amine $M(NR^1H)_p$, wherein p=1, 2, 3, 4, 5 or 6 to obtain a carboxy ester or a carboxy amide, and
ii) reacting the carboxy ester or carboxy amide with a (meth)acrylate monomer comprising an epoxide group or an oxetane group to obtain a curable (meth)acrylate resin for dental compositions.

13. The method of claim 12, wherein the M group is derived from methanol, ethanol, 1-butanol, 2-propanol, 2-methyl-1-propanol, 2-butanol, 2-methyl-1-butanol, benzyl alcohol, 1-phenethyl alcohol, 2-phenethyl alcohol, 2-phenyl-1-propanol, phenol, polyester polyol, polycarbonate polyol, polyurethane polyol, polycaprolactone polyol, methylamine, 1-aminoethane, 1-aminobutane, or 1,6-hexanediamine.

14. The method of claim 12, wherein M is phenyl, $C_1$-$C_3$ alkylphenyl, or $C_5$-$C_{14}$ alkylene.

15. A method of making a curable (meth)acrylate resin for dental compositions, comprising:
i) reacting an anhydride with an alcohol $M(OH)_p$ or an amine $M(NR^1H)_p$, wherein p=1, 2, 3, 4, 5, or 6, M is phenyl, $C_1$-$C_3$ alkylphenyl, and $C_5$-$C_{14}$ alkylene, and $R^1$ is hydrogen, a substituted or unsubstituted alkyl, alkenyl, aryl, or -alkylaryl group to obtain a carboxy ester or a carboxy amide; and
ii) reacting the carboxy ester or carboxy amide with a (meth)acrylate monomer comprising an epoxide group or an oxetane group to obtain a curable (meth)acrylate resin according to Structure IIIa

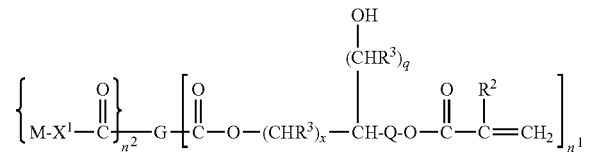

(IIIa)

wherein
M is selected from the group consisting of phenyl, $C_1$-$C_3$ alkylphenyl, and $C_5$-$C_{14}$ alkylene;
G is an aromatic hydrocarbyl group;
$X^1$ is O or —$NR^1$;
Q is substituted or unsubstituted $C_1$-$C_{16}$ alkylene, arylene, —$C_1$-$C_4$ alkyl-aryl-$C_1$-$C_4$ alkyl-, or polyether, wherein when Q is substituted, the substituents are selected from the group consisting of cyano, hydroxyl, nitro, azido, alkanoyl, carboxamido, alkyl, alkoxy, aryloxy, alkylthio, alkylsulfinyl, alkylsulfonyl, aminoalkyl, aryl, alkylaryl, arylalkoxy, aromatic heterocyclic, and combinations thereof;

$R^1$ is hydrogen, a substituted or unsubstituted alkyl, alkenyl, aryl, or -alkylaryl group, wherein when $R^1$ is substituted, substituents are selected from the group consisting of alkyl, aryl, alkylaryl, arylalkoxy, aromatic heterocyclic, and combinations thereof;

$R^2$ is H or methyl;

each instance of $R^3$ is independently hydrogen or $C_1$-$C_{12}$ alkyl;

x is 1 or 2;

q is 0 or 1;

$n^1$ is 2; and $n^2$ is 1 or 2;

wherein the curable (meth)acrylate resin is free of units derived from bisphenol A or bisphenol A analogs.

16. The method of claim 15, wherein the anhydride is trimellitic anhydride, pyromellitic dianhydride, 3,3',4,4' benzophenone tetracarboxylic dianhydride, biphenyl tetracarboxylic dianhydride, or a combination of the foregoing anhydrides.

17. The method of claim 15, wherein the alcohol is methanol, ethanol, 1-butanol, 2-propanol, 2-methyl-1-propanol, 2-butanol, 2-methyl-1-butanol, benzyl alcohol, 1-phenethyl alcohol, 2-phenethyl alcohol, 2-phenyl-1-propanol, or phenol; and wherein the amine is methylamine, 1-aminoethane, 1-aminobutane, or 1,6-hexanediamine.

18. The method of claim 15, wherein the (meth)acrylate monomer comprising an epoxide group or an oxetane group comprises a structure

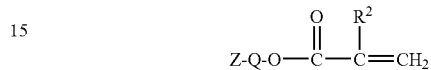

wherein Z is an epoxide or an oxetane group.

19. A curable (meth)acrylate resin for dental compositions, comprising:

a compound according to Structure IV:

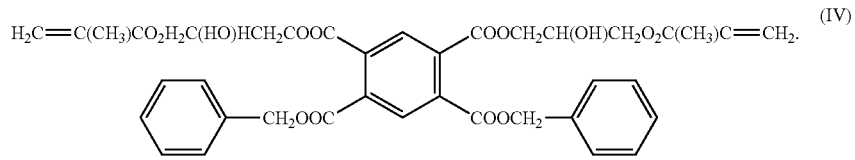

20. A dental resin composition comprising the curable resin of claim 19, a co-polymerizable ethylenically unsaturated oligomer, a polymerization initiator, an optional polymerization accelerator, an optional filler, and an optional diluent monomer, wherein the curable resin is present in an amount of about 50 to about 99 weight percent based on the total weight of polymerizable components.

* * * * *